(12) United States Patent
Armstrong et al.

(10) Patent No.: US 6,791,013 B2
(45) Date of Patent: Sep. 14, 2004

(54) MAIZE MIP SYNTHASE PROMOTER

(75) Inventors: Katherine Armstrong, Zionsville, IN (US); Timothy D. Hey, Zionsville, IN (US); Otto Folkerts, Guilford, CT (US); Kelley A. Smith, Lebanon, IN (US); Nicole L. Hopkins, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/727,628

(22) Filed: Dec. 1, 2000

(65) Prior Publication Data

US 2002/0068359 A1 Jun. 6, 2002

Related U.S. Application Data

(60) Provisional application No. 60/168,612, filed on Dec. 2, 1999.

(51) Int. Cl.[7] .............................. A01H 5/00; A01H 5/10; C12N 15/82; C12N 15/11
(52) U.S. Cl. ...................... 800/298; 536/24.1; 800/287; 435/320.1; 435/419
(58) Field of Search ............................. 435/320.1, 419, 435/468, 430; 800/287, 298, 260; 536/24.1, 23.2, 23.6

(56) References Cited

U.S. PATENT DOCUMENTS 6,225,529 B1 * 5/2001 Lappegard et al. ......... 800/287

OTHER PUBLICATIONS

Nelson et al., Regulation of Cell–Specific Inositol Metabolism and Transport in Plant Salinity Tolerance, May 1998, The Plant Cell, vol. 10, No. 5, pp. 753–764.*
Maiti et al., Promoter/leader deletion analysis and plant expression vector with the figwort mosaic virus (FMV)..., 1997, Transgenic Research, vol. 6, pp. 143–156.*
Donal et al., Mutation of either G box or I box sequence profoundly affects expression from the Arabidopsis rbcS–1A promoter, 1990, The EMBO Journal, vol. 9, No. 6, pp. 1717–1726.*
Lopes et al., Analysis of sequence in the INO1 promoter that are involved in its regulation by phospholipid precursors, 1991, Nucleic Acid Research, vol. 19, No. 7, pp. 1687–1693.*
Leppegard, US–09–377–648–7.*

* cited by examiner

Primary Examiner—Anne Kubelik
(74) Attorney, Agent, or Firm—Kenneth B. Ludwig; Donald R. Stuart

(57) ABSTRACT

The maize myo-inositol-1-phosphate synthase (MIP synthase) promoter is a novel embryo specific regulatory sequence useful in expressing heterologous nucleic acids in plants.

9 Claims, No Drawings

MAIZE MIP SYNTHASE PROMOTER

RELATED APPLICATION

This application claims priority from U.S. Provisional Patent Application Ser. No. 60/168,612, filed Dec. 2, 1999.

FIELD OF THE INVENTION

The invention provides DNA sequences and constructs that are useful in genetic engineering of plants. More particularly, the invention provides an isolated DNA sequence encoding maize myo-inositol-1-phosphate synthase (MIP synthase) and novel regulatory sequences derived from the MIP synthase gene, that can be used to drive expression of a variety of nucleic acid sequences in embryo tissue of transgenic plants.

BACKGROUND OF THE INVENTION

Plant genetic engineering projects require access to a variety of genetic elements that are used to regulate transgene expression. A primary example is the promoter, which regulates initiation of transcription.

A need exists for a variety of promoters for use in genetic engineering of plants. In particular, a need exists for promoters that drive expression specifically in embryo tissue.

BRIEF DESCRIPTION OF THE SEQUENCES

SEQ ID NO:1 is the DNA sequence for maize MIP synthase.

SEQ ID NO:2 is the amino acid sequence for maize MIP synthase.

SEQ ID NO:3 is the DNA sequence for the embryo specific maize MIP synthase promoter.

SUMMARY OF THE INVENTION

The invention provides an isolated DNA molecule encoding maize MIP synthase.

In another of its aspects, the invention provides embryo specific maize MIP synthase promoters corresponding to or derived from SEQ ID NO:3.

In another of its aspects, the invention provides a DNA construct comprising, operatively linked in the 5' to 3' direction, a) a maize MIP synthase promoter;
b) a DNA sequence of interest; and
c) a 3'UTR.

In another of its aspects, the invention provides a plasmid comprising a maize MIP synthase promoter, preferably bp 7-2064 of SEQ ID NO 3.

In another of its aspects, the invention provides a transformed plant comprising at least one plant cell that contains a DNA construct of the invention. The plant may be a monocot or dicot. Preferred plants are maize, rice, cotton and tobacco.

In another of its aspects, the invention provides seed or grain that contains a DNA construct of the invention.

DETAILED DESCRIPTION OF THE INVENTION

The DNA sequence of interest used in constructs of the invention may be any gene that it is desired to express or down regulate in plants. Particularly useful genes are those that confer tolerance to herbicides, insects, or viruses, and genes that provide improved nutritional value or processing characteristics of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. As is readily understood by those skilled in the art, any agronomically important gene conferring a desired trait or producing an important protein can be used.

The 3' UTR, or 3' untranslated region, employed in constructs of the invention is one that confers efficient processing of the mRNA, maintains stability of the message and directs the addition of adenosine ribonucleotides to the 3' end of the transcribed mRNA sequence. The 3' UTR may be native with the promoter region, native with the structural gene, or may be derived from another source. A wide variety of termination regions are available that may be obtained from genes capable of expression in plant hosts, e.g., bacterial, opine, viral, and plant genes. Suitable 3' UTRs include but are, not limited to: the per5 3' UTR (WO98/56921), the 3' UTR of the nopaline synthase (nos) gene, tmL 3', or acp 3', for example.

The present invention is generally applicable to the expression of structural genes in both monocotyledonous and dicotyledonous plants. This invention is particularly suitable for any member of the monocotyledonous (monocot) plant family including, but not limited to, maize, rice, barley, oats, wheat, sorghum, rye, sugarcane, pineapple, yams, onion, banana, coconut, and dates. A preferred application of the invention is in production of transgenic maize plants. The invention is particularly applicable to the family Graminaceae, in particular to maize, wheat, rice, oat, barley and sorghum. Dicotyledonous species include tobacco, tomato, sunflower, cotton, sugarbeet, potato, lettuce, melon, soybean and canola (rapeseed).

The present invention also includes DNA sequences having substantial sequence homology with the specifically disclosed regulatory sequences, such that they are able to have the disclosed effect on expression.

As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art.

It is contemplated that sequences corresponding to the above noted sequences may contain one or more modifications in the sequences from the wild-type but will still render the respective elements comparable with respect to the teachings of this invention. For example, as noted above, fragments may be used. One may incorporate modifications into the isolated sequences including the addition, deletion, or nonconservative substitution of a limited number of various nucleotides or the conservative substitution of many nucleotides. Further, the construction of such DNA molecules can employ sources which have been shown to confer enhancement of expression of heterologous genes placed under their regulatory control. Exemplary techniques for modifying oligonucleotide sequences include using polynucleotide-mediated, site-directed mutagenesis. See Zoller et al. (1984), DNA, 3:479–488; Higuchi et al. (1988), Nucl. Acids Res., 16:7351–7367, Ho et al. (1989), Gene, 77:51–59, Horton et al. (1989), Gene, 77:61; and PCR Technology: Principles and Applications for DNA Amplification, (ed.) Erlich (1989)).

Conventional technologies for introducing biological material into host cells include electroporation (see Shigekawa and Dower (1988), Biotechniques, 6:742; Miller, et al. (1988), Proc. Natl. Acad. Sci. USA, 85:856–860; and Powell, et al (1988), Appl. Environ. Microbiol., 54:655–660); direct DNA uptake mechanisms (see Mandel and Higa (1972), J. Mol. Biol., 53:159–162; Dityatkin, et al. (1972), Biochimica et Biophysica Acta, 281:319–323; Wigler, et al. (1979), Cell, 16:77; and Uchimiya, et al. (1982), In: Proc. 5th Intl. Cong. Plant Tissue and Cell Culture, A. Fujiwara (ed.), Jap. Assoc. for Plant Tissue Culture, Tokyo, pp. 507–508); fusion mechanisms (see Uchidaz, et al. (1980), In: Introduction of Macromolecules Into Viable Mammalian Cells, Baserga et al. (eds.) Wistar Symposium Series, 1:169–185); infectious agents (see Fraley, et al. (1986), CRC Crit. Rev. Plant Sci., 4:1–46); and Anderson (1984), Science, 226:401–409); microinjection mechanisms (see Crossway, et al. (1986), Mol. Gen. Genet., 202:179–185); and high velocity projectile mechanisms (see EPO 0 405 696 to Miller, Schuchardt, Skokut and Gould, (The Dow Chemical Company)

The appropriate procedure to transform a selected host cell may be chosen in accordance with the host cell used. Based on the experience to date, there appears to be little difference in the expression of genes, once inserted into cells, attributable to the method of transformation itself. Once introduced into the plant tissue, the expression of the structural gene may be assayed in a transient expression system, or it may be determined after selection for stable integration within the plant genome.

Techniques are known for the in vitro culture of plant tissue, and, in a number of cases, for regeneration into whole plants. The appropriate procedure to produce mature transgenic plants may be chosen in accordance with the plant species used. Regeneration varies from species to species of plants. Efficient regeneration will depend upon the medium, on the genotype, and on the history of the culture. Once whole plants have been obtained, they can be sexually or clonally reproduced in such a manner that at least one copy of the sequence is present in the cells of the progeny. Seed from the regenerated plants can be collected for future use, and plants grown from this seed. Procedures for transferring the introduced gene from the originally transformed plant into commercially useful cultivars are known to those skilled in the art.

In one of its aspects, the invention is regarded as encompassing any deleted version of the MIP synthase promoter that provides a functional plant promoter. Such promoters are encompassed by the term "MIP synthase promoter". A sequence will be regarded as providing a "functional" promoter for purposes of this application if it gives transient GUS expression above background levels when tested as in Example 4. Those skilled in the art will understand that various deletions from the 2058 bp sequence (bp 7-2064 of SEQ ID NO:3) can be made without destroying functionality of the sequence as a promoter. Deletion experiments are within the skill in the art. Preferably, a promoter of the invention will comprise 200 contiguous base pairs that are identical to 200 contiguous base pairs of the sequence defined by bp 7-2064 of SEQ ID NO:3. More preferable are promoters that comprise 500 contiguous base pairs that are identical to 500 contiguous base pairs of the sequence defined by bp 7-2064 of SEQ ID NO:3.

In the following examples, standard methods of DNA purification, restriction enzyme digestion, agarose gel analysis, DNA fragment isolation, ligation and transformation were used, as described in Sambrook, J., Fritsch, E. F., and Maniatis, T. (1989); Molecular Cloning a Laboratory Manual, second edition. (Cold Spring Harbor: Cold Spring Harbor Laboratory Press), Ausubel, F. M., Brent, R., Kingston, R., Moore, D., Smith, J., Seidman, J., and Struhl, K., eds. (1987); and Current Protocols in Molecular Biology. (New York: John Wiley and Sons).

EXAMPLE 1

Cloning of a Maize cDNA Encoding MIP Synthase
A. Isolation of a Maize MIP Synthase Probe Using Degenerate Primers A probe was isolated by PCR amplification of maize embryo cDNA using degenerate primers designed from the yeast MIP synthase amino acid sequence. At the time only the yeast MIP synthase sequence was known (Johnson, M. and Henry, S. (1989). Biosynthesis of Inositol in Yeast: Primary Structure of Myo-Inositol-1-Phosphate Synthase (EC 5.5.1.4) and Functional Analysis of its Structural Gene, the INO1 Locus. J. Biol. Chem. 264: 1274–1283.), it was not possible to identify "conserved" regions of the MIP synthase protein sequence. As an alternative, those amino acids that are encoded by only one or two codons were identified in the yeast protein sequence. Stretches of five or more of these low redundancy amino acids were selected as regions for primer design.

A clone (MP18) that could be translated into protein that had identity with yeast MIP synthase was identified. The insert of MIP18 was gel purified, labeled with $^{32}P$ and used to probe a lambda maize embryo cDNA library.

B. Isolation of a Maize MIP Positive cDNAs

Protocols for phage plating, plaque purification and in vivo excisions were as recommended by the manufacturer (Stratagene, LaJolla Calif.). Some changes were introduced and are noted below.

E. coli XL-1 blue were grown in NZY media containing 0.2% maltose to an optical density of 1.0 at 520 nm. The cells were collected by centrifugation at low speed and resuspended to the same density in 10 mM $MgSO_4$. Cells were stored for several days at 4° C. with little loss in plaque forming efficiency. Phage were preabsorbed to 200 µL of cells for 15 minutes at room temperature in Falcon 2059 tubes followed by 15 minutes at 37° C. The cells were plated in 3 mL NZY agarose at 48° C. on to NZY plates. Plates were incubated at 37° C. overnight.

Plates were chilled, 0.22 micron nylon filters were gently applied to the plate and allowed to absorb phage for 2 minutes. The filters were transferred to blotting paper saturated with 0.5 M NaOH, 1.5 M NaCl for 5 minutes. The filters were allowed to dry for 5 minutes then transferred to blotting paper saturated with a neutralization solution of 0.5M Tris pH 7.6, 1.5M NaCl for 15 minutes. The filters were then cross-linked using a Stratagene UV cross-linker on the "auto" setting. The filters were washed with two changes of 2×SSC, 0.1% SDS. Prehybridization was a minimum of 6 hours in 6×SSC, 10×Denhardt's solution, 0.1% SDS, 200 mg/mL DNA at 42° C.

DNA fragments were isolated using the Qiaex purification methods of Qiagen Inc., (Chatsworth, Calif.). The Boehringer Mannheim Random Primed DNA Labeling Kit (Indianapolis, Ind.) was used following manufacturer's instructions. Unincorporated nucleotides were removed by gel filtration through a Stratagene PUSH column following manufacturer's recommendations.

Hybridization solution for low stringency hybridization was 6×SSC, 10×Denhardt's solution, 0.1% SDS, 200 mg/mL DNA, 42° C., 6 hours. Low stringency washes were 40° C., 6×SSC, 1% SDS, 4 changes in a total of 2 liters. Hybridization solution for high stringency was as above except adjusted to 50% deionized formamide. Wash conditions were 0.1% SSC, 0.1% SDS, 60° C., 4 changes in a total of 2 liters.

The primary screen yielded many positive plaques that appeared on duplicate filters. The frequency of positive plaques approached 1% indicating that the gene was highly expressed in embryo. Several plaques were picked and screened a second and third time. Eight single plaques were picked from pure stocks and the plasmids rescued for cDNA insert analysis.

The eight MIP synthase positive clones were digested with restriction endonucleases Eco RI and Xho I to release the inserts from the vector. Based on the yeast sequence, a cDNA insert of approximately 2 kb was expected, this includes 500 amino acids of coding capacity and several hundred base pairs of nontranslated sequence. Two clones contained inserts that comigrated with the 2 kb marker. The other six clones contained inserts significantly smaller in size and were not characterized further. One clone with a cDNA insert of approximately 2 kb was chosen for DNA sequence analysis, it was called clone pMIP-7.

C. DNA Sequence Analysis of Maize MIP Synthase cDNA

The DNA sequence and the deduced amino acid sequence for the maize MIP synthase is shown in SEQ ID NO:1. The cDNA is 1959 nucleotides in length. The 5' most ATG is located at position 137 giving a putative 5' noncoding region of 136 nucleotides. A large open reading frame extends from the ATG at position 137 to a stop codon at position 1667. The reading frame encodes a polypeptide of 510 amino acids. A stop codon is located at position 1667 followed by 248 nucleotides of 3' nontranslated region. A short poly (A) tract is located at position 1918.

EXAMPLE 2

Analysis of Tissue Specific and Developmental Patterns in Seed

Mycogen proprietary maize genotypes CS608, HO1, CQ806, OQ414, and HiII, and a commonly available inbred B73, were grown under standard greenhouse conditions. For analysis of tissue specific gene expression of the MIP synthase promoter, tissues were harvested at the developmental times of interest and frozen at −70° C. until RNA extraction. For determination of the temporal expression pattern of MIP in seed embryos, kernels were dissected from ears of CQ806 and HO1 at different days after pollination (DAP). Following harvest, kernels were immediately dissected, embryos were collected and frozen in 50 ml conical tubes on dry ice. RNA was extracted and prepared for northern analysis using standard techniques. A MIP synthase hybridization probe was prepared from plasmid pMIP7 (for a description see Example 1) by digestion with EcoR1 and Xho1, followed by gel purification of the approximately 1950 bp insert. Twenty-five nanogram of gel-purified fragment was labeled with 50 µCi [α-32P]-dCTP (NEN Research Products) using READY-TO-GO labeling beads (Pharmacia) according to the manufacturer and purified over NUCTRAP push columns (Stratagene). The labeled probe was denatured by boiling for 5 min, chilled on ice for 5 min, and added directly to the prehybridized blots. Hybridization was done in SEAL-A-MEAL bags (DAZEY Corp., Industrial Airport, KA), at 42° C. for 16 h. Blots were washed six times for 30 min in large excess (500 mL) of pre-warmed washing solution [20 mM sodium phosphate pH6.5, 50 mM NaCl, 1 mM EDTA, and 0.1% SDS] at 60° C. Hybridization results indicated that MIP synthase was expressed in embryo tissues from each of the maize genotypes tested. Maximum expression in the embryos was observed 18–27 DAP. No significant expression was observed in leaves or roots. These data suggested that expression of MIP synthase was preferentially regulated in embryo tissues.

EXAMPLE 3

Cloning of the 5' Untranslated Regions from the Maize MIP Synthase Gene

The maize MIP synthase 5' flanking sequences were isolated from maize genomic DNA, var. OQ414 (proprietary line of Agrigenetics Inc., d/b/a Mycogen Seeds). DNA sequencing was accomplished using the ABI Prism DNA Sequencing Kit with AmpliTaq® Polymerase FS as described by the manufacturer (Perkin Elmer/Applied Biosystems Division, Foster City, Calif.). Sequencing reactions were run on an Applied Biosystem 373A DNA sequencer (Perkin Elmer/Applied Biosystems Division). The DNA sequence for the MIP synthase promoter is given in SEQ ID NO:3.

DESCRIPTION OF VECTORS

Four expression vectors were constructed which incorporated the MIP synthase promoter upstream from the β-glucuronidase (GUS) gene on a pUC19 backbone.

pMipGP339-1 and pMipGN345-1 were designed to test GUS expression in transient assays. The difference between these two vectors was that different 3' untranslated sequences were used as transcription terminators. pMipGP339-1 used the per5 3'UTR; pMipGN345-1 used the nos 3'UTR.

pMipGP341 and pMipGN350-1 are derivatives of pMipGP339-1 and pMipGN345-1 that add a selectable marker gene (phosphinotricin acetyl transferase (BAR) gene of *Streptomyces hygroscopicus* (White et al., (1989) Nucleic Acids Res. 18:1062)) driven by a double enhanced 35S promoter. pMipGP341 and pMipGN350-1 were used to test the MIP synthase promoter/GUS fusions in stably transformed maize embryos.

Plasmid UGP232-4 was used as a positive control in the transient expression studies. UGP232-4 is similar to pMipGP339, except that the GUS gene is driven by the ubiquitin 1 (ubi) promoter and intron I from maize in place of the MIP synthase promoter.

Plasmid pDAB305 was used as a control in the transient expression studies to standardize GUS expression across multiple experiments. pDAB305 is similar to pMipGN345-1, but uses the double enhanced 35S promoter used in pMipGN350-1 to drive expression of the GUS gene.

Production of the GUS protein from genes controlled by different promoter versions was often compared relative to an internal control gene that produced firefly luciferase (De Wet et al. (1987). Mol. Cell. Biol. 7(2), 725–37). A plasmid (pT3/T7-1 LUC) containing the luciferase (LUC) coding region was purchased from CLONTECH (Palo Alto, Calif.), and the coding region was modified at its 5' and 3' ends by standard methods to permit the isolation of the intact luciferase coding region on a 1702 bp fragment following digestion by NcoI and BglII. This fragment was used to replace the GUS gene of plasmid pDAB305, so that the luciferase coding region was expressed from the enhanced 35S promoter, resulting in plasmid pDeLux.

EXAMPLE 4

Transient Testing of Mip Synthase-Gus Constructs

A. Transient Histochemical GUS Expression in Embryos.

Three single gene plasmids were used for testing transient expression of GUS driven by the MIP synthase promoter in maize embryos. pUGP232-4 (encoding the maize ubiquitin promoter fused to GUS with the per5 3' UTR) served as a positive control. pMipGP339-1 and pMipGN345-1 contained a MIP synthase promoter-GUS fusion with the per5 and Nos 3' ends, respectively. Immature zygotic embryos from the "Hi-II" genotype (Armstrong et al. (1991) Maize Genet. Coop. News Lett. 65:92–93) were harvested at 12, 18, and 20 days after pollination (DAP). The embryos were cultured one to two days on 15Ag10 callus initiation medium consisting of N6 salts and vitamins (Chu et al, (1978) *The N6 medium and its application to anther culture of cereal crops*. Proc. Symp. Plant Tissue Culture, Peking Press, 43–56), 1.0 mg/L 2,4-dichlorophenoxyacetic acid (2,4-D), 25 mM L-proline, 100 mg/L casein hydrolysate, 10 mg/L $AgNO_3$, 2.5 g/L GELRITE (Schweizerhall, South Plainfield, N.J.), and 20 g/L sucrose, with a pH of 5.8 prior to autoclaving. Before transformation, the embryos were transferred to 15Ag10+SM medium (15Ag10 with 0.2 M sorbitol and 0.2 M mannitol) for four hours of osmotic pretreatment. For helium blasting, 12 embryos were arranged in a target area of approximately 1 $cm^2$ on blasting medium and covered with a 230 µm mesh stainless steel screen. Blasting medium differed from 15Ag10+SM medium in that it lacked silver nitrate, contained only 6 mM L-proline and was solidified with 20 g/L TC agar (PhytoTechnology Laboratories, LLC, Shawnee Mission, Kans.).

DNA was prepared for blasting using equal molar amounts of the GUS plasmids. A total of 70 µg of DNA, test DNA plus Bluescript™ DNA (Stratagene, La Jolla, Calif.) when necessary, was diluted in sterile water to a volume of 150 µL. The DNA and water were added to 30 mg of surface-sterilized 1.0 µm spherical gold particles (Bio-Rad Laboratories, Hercules, Calif.). The mixture was vortexed briefly (approximately 15 seconds) before adding 37 µL of 2.5 M calcium chloride and 15 µL of 0.1 M spermidine (free base). After vortexing for 30 seconds, the DNA and gold were allowed to precipitate from solution. The supernatant was removed and 1 mL of ethanol was added. The DNA/gold mixture was diluted 1:4 before use for transformation.

Helium blasting accelerated suspended DNA-coated gold particles toward and into the prepared tissue targets. The device used was an earlier prototype of that described in U.S. Pat. No. 5,141,131 which is incorporated herein by reference. Tissues were placed under a partial vacuum of 25 inches of Hg in the device chamber. DNA-coated gold particles were accelerated at each embryo target once using a helium pressure of 1500 psi, with each blast delivering 20 µL of the DNA/gold suspension. Following blasting, the embryos were transferred back to 15Ag10+SM medium and incubated in the dark at 27° C. for 18–24 hours prior to GUS histochemical assay.

Embryos were subjected to histochemical GUS analysis (Jefferson (1987) Plant Mol. Biol. Rep. 5:387–405) by placing in 24-well microtiter plates containing 250–500 µL of assay buffer [0.1 M sodium phosphate, pH 8.0, 0.5 mM potassium ferricyanide, 0.5 mM potassium ferrocyanide, 10 mM disodium EDTA, 0.95 mM 5-bromo-4-chloro-3-indolyl-beta-D-glucuronide, and 0.6% (v/v) TRITON X-100] per well. A partial vacuum was drawn for 2–15 minutes prior to being incubated in the dark for 24–48 hours at 37° C.

Table 3 summarizes results of three experiments testing transient GUS expression of the MIP-synthase promoter in comparison to a maize ubiquitin control. Three to five targets (12 embryos/target) were blasted per construct in each experiment. Though not as intense as the control, the MIP synthase construct with the per5 3'UTR resulted in GUS expression in embryos harvested at 12, 18, and 20 DAP. The MIP synthase plasmid with the Nos 3'end also demonstrated GUS activity in 20 DAP embryos. In conclusion, moderate levels of transient expression were observed with the MIP synthase promoter in immature zygotic embryos of maize.

TABLE 3

Transient GUS Expression of MIP Synthase-GUS Constructs in Maize Embryos

| Days after Pollination | Plasmid | | |
|---|---|---|---|
| | pUGP232-4 | pMipGP339-1 | pMipGN345-1 |
| 12 | +++ | + | nt |
| 18 | +++ | ++ | nt |
| 20 | +++ | + to ++ | + | nt = not tested

B. Transient Quantitative GUS Expression in Maize Regenerable Callus.

Plasmids pMipGP339-1 and pMipGN345-1 were tested in regenerable maize callus for an indication of the level to which the MIP synthase promoter drives constitutive expression. A modified 35S promoter/GUS construct (pDAB305), which is highly expressed in maize, was used as a control. Expression of GUS driven by either pMipGP339-1 or pMipGN345-1 was determined as a percent of GUS driven by pDAB305.

pMipGP339-1 and pMipGN345-1 each resulted in expression 3% of pDAB305 which was statistically different from the control. In conjunction with the embryo data above, the insignificant constitutive expression strongly indicates MIP synthase as an embryo specific promoter.

EXAMPLE 5

Production of Stably Transformed Maize Callus

Type II callus cultures were initiated from immature zygotic embryos of the genotype "Hi-II." (Armstrong et al, (1991) Maize Genet. Coop. Newslett., 65: 92–93). Embryos were isolated from greenhouse-grown ears from crosses between Hi-II parent A and Hi-II parent B or $F_2$ embryos derived from a self- or sib-pollination of a Hi-II plant. Immature embryos (1.5 to 3.5 mm) were cultured on 15Ag10 callus initiation medium as described herein. After four to six weeks callus was subcultured onto callus maintenance medium (initiation medium in which $AgNO_3$ was omitted and L-proline was reduced to 6 mM) Selection for Type II callus took place for ca. 12–16 weeks.

Plasmids pMipGN350-1 and pMipGP341 were independently transformed into embryogenic callus tissue. In preparation for helium blasting, 140 μg of plasmid DNA was precipitated onto 60 mg of alcohol-rinsed, spherical gold particles (1.5–3.0 μm diameter, Aldrich Chemical Co., Inc., Milwaukee, Wis.) by adding 74 μL of 2.5M $CaCl_2$ $H_2O$ and 30 μL of 0.1M spermidine (free base) to 300 μL of plasmid DNA and $H_2O$. The solution was immediately vortexed and the DNA-coated gold particles were allowed to settle. The resulting clear supernatant was removed and the gold particles were resuspended in 1 ml of absolute ethanol. This suspension was diluted with absolute ethanol to obtain 15 mg DNA-coated gold/mL.

Approximately 600 mg of embryogenic callus tissue was spread over the surface of Type II osmotic medium as described herein. Following a 4 hour pre-treatment, tissue was transferred to culture dishes containing blasting medium as described herein. Targets were individually blasted with DNA/gold mixture using the helium blast device described herein. Tissues were covered with a stainless steel screen (104 μm openings) and placed under a partial vacuum of 25 inches of Hg in the device chamber. The DNA-coated gold particles were further diluted 1:1 with absolute ethanol prior to blasting and were accelerated at the callus targets four times using a helium pressure of 1500 psi, with each blast delivering 20 μL of the DNA/gold suspension. The targets were rotated 180° after each blast. The tissue was also mixed halfway through the procedure to expose unblasted callus. Immediately post-blasting, the tissue was transferred back to Type II osmotic medium for a 16–24 h recovery period. Afterwards, the tissue was divided into small pieces and transferred to selection medium (maintenance medium lacking casein hydrolysate and L-proline but containing 30 mg/L BASTA® (AgrEvo, Berlin, Germany)). Every four weeks for three months, tissue pieces were non-selectively transferred to fresh selection medium. After 9 weeks and up to 21 weeks in selection, callus sectors found proliferating against a background of growth-inhibited tissue were removed and isolated. The resulting BASTA®-resistant tissue was subcultured biweekly onto fresh selection medium.

EXAMPLE 6

Development of Mature Somatic Embryos and Regeneration of Transgenic Plants

From these stably transformed cultures, somatic embryos were induced to develop as seed embryos by growing embryogenic callus on Murashige and Skoog basal medium, hereinafter MS medium (Murashige and Skoog, Physiol. Plant. (1962) 15: 473–497) containing 60 g/L sucrose. The callus was grown for seven days, and then somatic embryos were individually transferred to MS medium containing 60 g/L sucrose and 10 μM abscisic acid, hereinafter ABA, for an additional 7 days. After 14 days of maturation, somatic embryos from different transgenic lines were assayed for histochemical expression of the GUS gene by placing in approximately 400 μL of GUS solution as described herein except without drawing a vacuum. GUS-expressing lines and non-GUS-expressing lines were identified and transferred to regeneration media. Regeneration was initiated by transferring embryogenic callus tissue to cytokinin-based induction medium, MS medium containing 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA®, and 2.5 g/L GELRITE at pH 5.7. The cultures were placed in low light (125 ft-candles) for one week followed by one week in high light (325 ft-candles). Following a two-week induction period, tissue was non-selectively transferred to hormone-free regeneration medium, which was identical to the induction medium except that it lacked 2,4-D and BAP, and was kept in high light. Small (3–5 cm) plantlets were removed and placed in 150×25 mm culture tubes containing Schenk and Hildebrandt salts and vitamins, hereinafter SH medium (Schenk and Hildebrandt, (1972) Can. J. Bot. 50:199–204), 10 g/L sucrose, 100 mg/L myo-inositol, and 2.5 g/L GELRITE, pH 5.8). At least one individual plantlet from each regenerable line was sacrificed for histochemical GUS assay. Intact plantlets (3–10 cm) were placed in 15 mL conical centrifuge tubes and submersed in approximately 5–10 mL GUS assay buffer and incubated as described herein. Non-assayed plantlets were transferred to 12 cm round pots containing approximately 0.25 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 6–8 leaf stage, plants were transplanted to five gallon pots containing approximately 4 kg METRO-MIX 360, and grown to maturity.

Primary regenerants were outcrossed with the elite inbred, OQ414. $R_1$ seed was collected approximately 6 weeks post-pollination.

A total of 312 Type II callus targets were blasted with pMipGN350-1 and pMipGP341. Thirty-six Basta®-resistant callus isolates were recovered from selection, however, only 29 were induced to form mature somatic embryos as described herein. Twenty-four of these events produced some level of blue staining following histochemical GUS assay, as described herein, ranging from very faint blue to a deep indigo blue. Thirteen of these expressers plus one maize ubiquitin/GUS/Nos positive control and one (non-GUS) transgenic negative control were regenerated. Approximately 16 $R_0$ plants were regenerated from each of these lines. Ten of the 13 MIP regenerants produced $R_1$ seed.

EXAMPLE 7

Gus Analysis of Transgenic Plants

A. GUS Analysis of Embryos.

Embryos from pMipGP341-06.06, pMipGN350-05.01, pMipGN350-14.01, 1817-02.11 (transgenic negative control), Whisker-12.12 and Whisker-12.14 (maize Ubiquitin-GUS positive controls) were harvested 10 through 30 days after pollination (DAP) at 5 day intervals. Up to 10 kernels were collected per ear at each harvest depending on seed set of the Ro plants. According to the method of Jefferson (1987) Plant Mol. Biol. Rep. 5:387–405 as described herein, embryos were histochemically examined for GUS expression.

No GUS expression was observed in embryos of the trangenic negative control (1817-02.11). Unexpectedly, GUS was not detected in embryos of the Ubiquitin positive controls (Whisker-12.12 and Whisker-12.14). The growth of these plants was stunted and seed set was poor. However, each of the three MIP synthase events demonstrated GUS expression in the $R_1$ embryos. In pMipGP341-06.06, expression was observed as early as 10 DAP. For the p350 events, GUS was detected first at 15 DAP. Expression in all lines continued through maturity at 30 DAP. Segregation generally followed Mendelian inheritance patterns.

B. GUS Analysis of Roots and Leaves.

Two plants per transgenic event, as well as two nontransformed controls (OQ414), transformed negative controls (1817-02 plants), and positive controls expressing maize Ubiquitin-driven GUS (Whisker-12 events) were sacrificed at different developmental stages. One plant per event at the V6 (6 leaf) and VT (emerging tassel) stages was harvested and the leaves and roots were separately pooled for analysis. Additionally, the sixth leaf of several plants per event was collected at the V6 stage and individually evaluated for GUS expression.

No GUS activity was detected in the leaves or roots of the nontransformed (OQ414) or transformed negative (1817-02) controls. Variable, yet significant, GUS expression was observed in the positive control (Whisker-12 event, seven plants), ranging from 0.45 to 2.34 ng GUS equivalent/µg protein in the leaves and 0.28 to 0.47 in the roots. The MIP synthase-GUS transgenic events demonstrated no significant GUS activity in leaves or roots, leading to the conclusion that the MIP synthase promoter is embryo specific.

What is claimed is:

1. An isolated nucleic acid molecule comprising bases 7-2064 of SEQ ID NO:3.

2. A nucleic acid construct comprising the isolated nucleic acid molecule of claim 1 operably linked to a heterologous nucleic acid.

3. An expression vector comprising the isolated nucleic acid molecule of claim 1.

4. A transformed plant cell comprising the expression vector of claim 3.

5. Seed or grain that comprises the isolated nucleic acid molecule of claim 1.

6. A transgenic plant comprising at least one plant cell that contains the isolated nucleic acid molecule of claim 1.

7. A method of producing plant tissue capable of expressing a heterologous nucleic acid, wherein the method comprises introducing into at least one plant cell of a plant tissue the construct of claim 2.

8. The method of claim 7, wherein the method further comprises regenerating said one plant cell into a plant.

9. The method of claim 8, wherein the method further comprises producing at least one progeny of said plant, wherein the progeny is selected for expression of the heterologous nucleic acid.

* * * * *

SEQUENCE LISTING

```
<160> NUMBER OF SEQ ID NOS: 3

<210> SEQ ID NO 1
<211> LENGTH: 1959
<212> TYPE: DNA
<213> ORGANISM: Zea mays
<220> FEATURE:
<221> NAME/KEY: CDS
<222> LOCATION: (137)..(1699)

<400> SEQUENCE: 1
gaattcggca caagcaaagg agcgcggcgg cccctccttc cttcctccca cttctctcgc      60
gcggcgctcg cttacctcgc ctcgcattcc gttcgagcag gggagcggca gtgagaaggg     120
agggaattaa ggcaag atg ttc atc gag agc ttc cgc gtc gag agc ccc cac    172
                  Met Phe Ile Glu Ser Phe Arg Val Glu Ser Pro His
                    1               5                  10 gtg cgg tac ggc ccg acg gag atc gag tcg gag tac cgg tac gac acg      220
Val Arg Tyr Gly Pro Thr Glu Ile Glu Ser Glu Tyr Arg Tyr Asp Thr
             15                  20                  25 acg gag ctg gtg cac gag gcc aag gac ggc gcc tcc cgc tgg gtc gtc      268
Thr Glu Leu Val His Glu Ala Lys Asp Gly Ala Ser Arg Trp Val Val
         30                  35                  40 cgc ccc aag tcc gtc aag tac aac ttc cgg acc agc acc gcg gtc ccc      316
Arg Pro Lys Ser Val Lys Tyr Asn Phe Arg Thr Ser Thr Ala Val Pro
 45                  50                  55                  60 aag ctc ggg gtc atg ctt gtg ggg tgg gga ggc aac aac ggg tcc acg      364
Lys Leu Gly Val Met Leu Val Gly Trp Gly Gly Asn Asn Gly Ser Thr
                 65                  70                  75 ctg acg gct ggg gtc att gcc aac agg gag ggg atc tca tgg gcg acc      412
Leu Thr Ala Gly Val Ile Ala Asn Arg Glu Gly Ile Ser Trp Ala Thr
             80                  85                  90 aag gac aag gtg cag caa gcc aac tac tac ggc tcc ctc acc cag gct      460
Lys Asp Lys Val Gln Gln Ala Asn Tyr Tyr Gly Ser Leu Thr Gln Ala
         95                 100                 105 tcc acc atc aga gta ggc agc tac aac ggg gag gag ata tat gcg ccg      508
Ser Thr Ile Arg Val Gly Ser Tyr Asn Gly Glu Glu Ile Tyr Ala Pro
    110                 115                 120 ttc aag agc ctc cta ccc atg gtg aac cca gac gac ctt gtg ttt gga      556
Phe Lys Ser Leu Leu Pro Met Val Asn Pro Asp Asp Leu Val Phe Gly
125                 130                 135                 140 ggc tgg gac atc agc agc atg aac ctg gca gat gcc atg acc agg gcc      604
Gly Trp Asp Ile Ser Ser Met Asn Leu Ala Asp Ala Met Thr Arg Ala
                145                 150                 155 aag gtg ctg gac att gac ctg cag aag cag ctc agg ccc tac atg gag      652
Lys Val Leu Asp Ile Asp Leu Gln Lys Gln Leu Arg Pro Tyr Met Glu
            160                 165                 170 tcc atg gtg cca ctt ccc ggt gtc tat gat ccg gac ttc atc gcc gct      700
```

-continued

```
Ser Met Val Pro Leu Pro Gly Val Tyr Asp Pro Asp Phe Ile Ala Ala
        175                 180                 185 aac cag ggc tct cgt gcc aac aat gtc atc aag ggc acc aag aaa gaa    748
Asn Gln Gly Ser Arg Ala Asn Asn Val Ile Lys Gly Thr Lys Lys Glu
        190                 195                 200 cag gtg gag cag atc atc aaa gat atc agg gag ttt aag gag aag aac    796
Gln Val Glu Gln Ile Ile Lys Asp Ile Arg Glu Phe Lys Glu Lys Asn
205                 210                 215                 220 aaa gtg gac aag gta gtt gtg ctg tgg act gca aac act gaa agg tac    844
Lys Val Asp Lys Val Val Val Leu Trp Thr Ala Asn Thr Glu Arg Tyr
                225                 230                 235 agc aat gta tgt gct ggt ctc aac gac aca atg gag aat ctg ctg gca    892
Ser Asn Val Cys Ala Gly Leu Asn Asp Thr Met Glu Asn Leu Leu Ala
                240                 245                 250 tct gtg gac aag aac gag gcg gag atc tcg cca tca aca cta tat gcc    940
Ser Val Asp Lys Asn Glu Ala Glu Ile Ser Pro Ser Thr Leu Tyr Ala
                255                 260                 265 att gcc tgt gtc acg gag ggg gtg ccg ttc atc aat ggg agc ccc cag    988
Ile Ala Cys Val Thr Glu Gly Val Pro Phe Ile Asn Gly Ser Pro Gln
        270                 275                 280 aac act ttt gtg cct ggg ctg att gat ctt gct atc aag aac aac tgc   1036
Asn Thr Phe Val Pro Gly Leu Ile Asp Leu Ala Ile Lys Asn Asn Cys
285                 290                 295                 300 ctg atc ggt ggt gac gac ttc aag agt ggg cag acc aag atg aaa tcg   1084
Leu Ile Gly Gly Asp Asp Phe Lys Ser Gly Gln Thr Lys Met Lys Ser
                305                 310                 315 gtc ctg gtt gat ttt ctt gtt ggt gct gga ata aag ccc acc tcg att   1132
Val Leu Val Asp Phe Leu Val Gly Ala Gly Ile Lys Pro Thr Ser Ile
                320                 325                 330 gtg agc tac aac cac ttg gga aac aac gac ggc atg aac ctg tct gcc   1180
Val Ser Tyr Asn His Leu Gly Asn Asn Asp Gly Met Asn Leu Ser Ala
                335                 340                 345 cct caa aca ttc agg tcc aag gag atc tcc aag agc aac gtg gtg gat   1228
Pro Gln Thr Phe Arg Ser Lys Glu Ile Ser Lys Ser Asn Val Val Asp
        350                 355                 360 gac atg gtc tca agc aat gcc att ctc tat ggg ccc ggc gag cat ccc   1276
Asp Met Val Ser Ser Asn Ala Ile Leu Tyr Gly Pro Gly Glu His Pro
365                 370                 375                 380 gat cat gtt gtt gtc atc aag tat gtg ccg tat gtg gga gac agt aag   1324
Asp His Val Val Val Ile Lys Tyr Val Pro Tyr Val Gly Asp Ser Lys
                385                 390                 395 agg gct atg gac gag tac aca tca gag atc ttc atg ggc ggc aag agc   1372
Arg Ala Met Asp Glu Tyr Thr Ser Glu Ile Phe Met Gly Gly Lys Ser
                400                 405                 410 acc atc gtg ctg cac aac acc tgc gag gac tcg ctc ctc gcc gca ccg   1420
Thr Ile Val Leu His Asn Thr Cys Glu Asp Ser Leu Leu Ala Ala Pro
                415                 420                 425 atc atc ctc gat ctg gtg ctc ctg gct gag ctc agc acc agg atc cag   1468
Ile Ile Leu Asp Leu Val Leu Leu Ala Glu Leu Ser Thr Arg Ile Gln
        430                 435                 440 tta aaa cct gag gga acg gac aag ttc cac tcc ttc cac ccg gtg gcc   1516
Leu Lys Pro Glu Gly Thr Asp Lys Phe His Ser Phe His Pro Val Ala
445                 450                 455                 460 acc atc ctt agc tac ctc acc aag gca cca ctg gtt cca ccc ggc aca   1564
Thr Ile Leu Ser Tyr Leu Thr Lys Ala Pro Leu Val Pro Pro Gly Thr
                465                 470                 475 ccg gtg gtg aac gct ctt gca aag cag agg gcg atg ctg gag aac atc   1612
Pro Val Val Asn Ala Leu Ala Lys Gln Arg Ala Met Leu Glu Asn Ile
                480                 485                 490
```

-continued

```
atg agg gct tgc gtt ggc ctg gcc cca gag aac aac atg atc ctg gag    1660
Met Arg Ala Cys Val Gly Leu Ala Pro Glu Asn Asn Met Ile Leu Glu
        495                 500                 505 tac aag tga gcg aag tgg cgt ggc ctg cag cta gat atg gaggaggctg     1709
Tyr Lys
    510 cacgaagggg actagagagg cgagattagc tgtggaattg tgttggcttc tcgtgttttc  1769 ttttgcgttc ttttcctggt catcgctgtg gcgcttttgt attttatttg ttggacccgt  1829 aacactatca gggctctgct attagcgctt gaagcctgta atggcattgg catcgtatga  1889 taatgtgatc gagggtgcta gttcccctaa aaaaaaaaa aaaaaaaaac tcgagggggg   1949 gcccggtacc                                                        1959

<210> SEQ ID NO 2
<211> LENGTH: 510
<212> TYPE: PRT
<213> ORGANISM: Zea mays

<400> SEQUENCE: 2

Met Phe Ile Glu Ser Phe Arg Val Glu Ser Pro His Val Arg Tyr Gly
 1               5                  10                  15

Pro Thr Glu Ile Glu Ser Glu Tyr Arg Tyr Asp Thr Thr Glu Leu Val
            20                  25                  30

His Glu Ala Lys Asp Gly Ala Ser Arg Trp Val Val Arg Pro Lys Ser
        35                  40                  45

Val Lys Tyr Asn Phe Arg Thr Ser Thr Ala Val Pro Lys Leu Gly Val
    50                  55                  60

Met Leu Val Gly Trp Gly Gly Asn Asn Gly Ser Thr Leu Thr Ala Gly
 65                  70                  75                  80

Val Ile Ala Asn Arg Glu Gly Ile Ser Trp Ala Thr Lys Asp Lys Val
                85                  90                  95

Gln Gln Ala Asn Tyr Tyr Gly Ser Leu Thr Gln Ala Ser Thr Ile Arg
            100                 105                 110

Val Gly Ser Tyr Asn Gly Glu Glu Ile Tyr Ala Pro Phe Lys Ser Leu
        115                 120                 125

Leu Pro Met Val Asn Pro Asp Asp Leu Val Phe Gly Gly Trp Asp Ile
    130                 135                 140

Ser Ser Met Asn Leu Ala Asp Ala Met Thr Arg Ala Lys Val Leu Asp
145                 150                 155                 160

Ile Asp Leu Gln Lys Gln Leu Arg Pro Tyr Met Glu Ser Met Val Pro
                165                 170                 175

Leu Pro Gly Val Tyr Asp Pro Asp Phe Ile Ala Ala Asn Gln Gly Ser
            180                 185                 190

Arg Ala Asn Asn Val Ile Lys Gly Thr Lys Lys Glu Gln Val Glu Gln
        195                 200                 205

Ile Ile Lys Asp Ile Arg Glu Phe Lys Glu Lys Asn Lys Val Asp Lys
    210                 215                 220

Val Val Val Leu Trp Thr Ala Asn Thr Glu Arg Tyr Ser Asn Val Cys
225                 230                 235                 240

Ala Gly Leu Asn Asp Thr Met Glu Asn Leu Leu Ala Ser Val Asp Lys
                245                 250                 255

Asn Glu Ala Glu Ile Ser Pro Ser Thr Leu Tyr Ala Ile Ala Cys Val
            260                 265                 270

Thr Glu Gly Val Pro Phe Ile Asn Gly Ser Pro Gln Asn Thr Phe Val
        275                 280                 285
```

```
Pro Gly Leu Ile Asp Leu Ala Ile Lys Asn Asn Cys Leu Ile Gly Gly
    290                 295                 300

Asp Asp Phe Lys Ser Gly Gln Thr Lys Met Lys Ser Val Leu Val Asp
305                 310                 315                 320

Phe Leu Val Gly Ala Gly Ile Lys Pro Thr Ser Ile Val Ser Tyr Asn
                325                 330                 335

His Leu Gly Asn Asn Asp Gly Met Asn Leu Ser Ala Pro Gln Thr Phe
            340                 345                 350

Arg Ser Lys Glu Ile Ser Lys Ser Asn Val Val Asp Asp Met Val Ser
        355                 360                 365

Ser Asn Ala Ile Leu Tyr Gly Pro Gly Glu His Pro Asp His Val Val
    370                 375                 380

Val Ile Lys Tyr Val Pro Tyr Val Gly Asp Ser Lys Arg Ala Met Asp
385                 390                 395                 400

Glu Tyr Thr Ser Glu Ile Phe Met Gly Gly Lys Ser Thr Ile Val Leu
                405                 410                 415

His Asn Thr Cys Glu Asp Ser Leu Leu Ala Ala Pro Ile Ile Leu Asp
            420                 425                 430

Leu Val Leu Leu Ala Glu Leu Ser Thr Arg Ile Gln Leu Lys Pro Glu
        435                 440                 445

Gly Thr Asp Lys Phe His Ser Phe His Pro Val Ala Thr Ile Leu Ser
    450                 455                 460

Tyr Leu Thr Lys Ala Pro Leu Val Pro Pro Gly Thr Pro Val Val Asn
465                 470                 475                 480

Ala Leu Ala Lys Gln Arg Ala Met Leu Glu Asn Ile Met Arg Ala Cys
                485                 490                 495

Val Gly Leu Ala Pro Glu Asn Asn Met Ile Leu Glu Tyr Lys
            500                 505                 510

<210> SEQ ID NO 3
<211> LENGTH: 2069
<212> TYPE: DNA
<213> ORGANISM: Zea mays

<400> SEQUENCE: 3
tctagatttt ttttcaattc accccgagta aatatccaat cacaatctaa aaatcaggag      60
aaattatatg gccatattat agaagcaact aaataaaatg tgcgttgtat tgaaaaaaaa     120
acctatttat aacaaacatc tgccaagaat acaattcttt tatacacaac ttatatgtga     180 gttcttttc tcttgtaact cttattaata aaacattttt ggctattaaa taatggcaac      240
taagttagca ccactgtaat tagattttgt ctggaacaat ttctctgact aagaagctat     300
ttggactgtc cttttgccaa acaagtagaa aatggaaccg ctccttaaaa aaccattctc     360
acatcgctgg gtgctgaata aaactgaaaa cattagcttt ttatagctct cgctctctgc     420
tagtatgtgt tataaaatca ttttaccaat tacctttta aataactgta cgtagtttca      480
tcagtagaac tactcacgga gctaaaacaa aaaagttgt tctactgata aaagcagaga      540
tgatgtatga ccgtgaccgt gagctaaagt ccaaaaaaaa aaactgctcc acaataacga     600 caaacaaag ttgtattgta tggcctaaat tacagcacac tgacaccaca cgtatattat      660
tctctctcca ttatcacagg atgtaactgt aaaaattttg tatgttaaac atttgtagta     720
aatattgcta gcatttacgt ctacggaatt tattgaaaaa atgtagtatt gttttatata     780
attttaataa aactgtaaat cgtctggctt cgtttctgga tggaggataa atagtgaata     840
```

-continued

```
cgaatgggaa acaccacaac aaccacgccg ctgcgttctg cgaatcacat gagcgatcag    900
tgccttgctg ttccgtgaac ttgcacgcaa ggacgagagc ctttctgcct ttgcatgcaa    960
ggacaagagt ctttacatgc aaggacaaat aactcccacg cgccccaccg tgctttggca   1020
agccacatgg caccctgccg atcacaattc acaggcccag gcttccggtg gtcgcgtgcc   1080
gtgagtctga caccgcacca catggccgcc gtaggccgtg cctacgcacc aaggcgactc   1140
gtggtgccag gctctcggcg gctttggagt cggtgccatg ccgcgggtc cgtggaccgc    1200
tcctagggc caggacgaag ctgcaccgca caagcgggcc gcgcgtgact ccgtgaccgt    1260
gaggcgggcg taaccaggag cttccgccac gcttgagacc acgtgacggc gcagaggagc   1320
tccacgcgat caaaagcgcc cgccacttct aaaggtcagg ggtcttgcgt tctgccctc    1380
gtgcttcctt caaattctgg acctagtgga tcaatttacg tacacctcag caaccgatgc   1440
agccagtatg atgagcacga ttgtgacgtg ttgggggtca tggtcaatgg caaccgagca   1500
cgaattggta gtgtctgctt tttgtacacg tgatagcatt tgattcgttc attcaatttg   1560
aactgtttaa acttatatat gtagagaaat tagtccaact catgcttaat aaaaagtata   1620
aaacccatcg aatttatgaa ttatgatagc aggtatccta tccattgtca tcgctcacag   1680
tcacagaggt agccactgcc gacggccgac ggcctcccat ttcgctcccc tcctactcct   1740
atgctgcggt ccagcaaaag ttcgggcctt ccggcaatcc gccggcgccc gtcggctcaa   1800
atcgcatcta ccgcggctag aagctctctc ttcctccctc cgatccggtg gggtccattt   1860
ccttcaattg tggcagtggc cgtctcgaac cctctataaa tcccccaccc cggacaccct   1920
tccccgacca cacagcccaa caacaaggag cgcggcggcc cctccttcct tcctcccact   1980
tctctcgcgc ggcgctcgct tacctcgcct cgcattccgt tcgagcaggg gagcggcagt   2040
gagaagggag ggaattaagg caaccatgg                                     2069
```